United States Patent [19]

Fernwood et al.

[11] Patent Number: 4,612,710

[45] Date of Patent: Sep. 23, 1986

[54] METHOD AND APPARATUS FOR DRYING GEL SLABS

[75] Inventors: George G. Fernwood, San Anselmo; Samuel Burd, Oakland, both of Calif.

[73] Assignee: Bio-Rad Laboratories, Inc., Richmond, Calif.

[21] Appl. No.: 653,971

[22] Filed: Sep. 20, 1984

[51] Int. Cl.[4] .............................................. F26B 7/00
[52] U.S. Cl. .......................................... 34/16; 34/92; 34/143; 34/148; 34/151; 219/524
[58] Field of Search ....................... 34/15, 16, 92, 148, 34/151, 143, 145; 219/345, 459, 520, 524, 533; 38/14, 15, 16

[56] References Cited

U.S. PATENT DOCUMENTS

| | | | |
|---|---|---|---|
| 1,536,637 | 5/1925 | Thurnauer | 38/14 |
| 2,653,394 | 9/1953 | Nelson et al. | 34/143 |
| 3,024,495 | 3/1962 | Thompson | 219/520 |
| 3,135,589 | 6/1964 | Stokes | 34/73 |
| 3,202,278 | 8/1965 | Taylor | 206/80 |
| 3,253,348 | 5/1966 | Oderman et al. | 34/46 |
| 3,253,351 | 5/1966 | Bettanin | 34/92 |
| 3,284,917 | 11/1966 | Foote | 34/21 |
| 3,715,818 | 2/1973 | Sassman | 38/15 |
| 3,889,389 | 6/1975 | Serup | 34/148 |
| 3,935,646 | 2/1976 | Grandine et al. | 34/92 |
| 3,968,581 | 7/1976 | Tsunoda | 38/15 |
| 4,020,563 | 5/1977 | Hoefer | 34/48 |
| 4,206,345 | 6/1980 | Maass et al. | 219/524 |
| 4,262,189 | 4/1981 | Eisenhoffer | 219/524 |
| 4,274,214 | 6/1981 | Hauser | 38/14 |
| 4,432,956 | 2/1984 | Zarzycki et al. | 423/338 |

OTHER PUBLICATIONS

H. R. Maurer et al., Polyacrylamide Gel Electrophoresis on Micro Slabs, *Analytical Biochemistry*, 46, 19–32 (1972).
R. Lim et al., Autoradiography with Acrylamide Gel Slab Electrophoresis, *Analytical Biochemistry*, 29, 48–57 (1969).
D. P. Borris et al., Dried Acrylamide Electrophoresis Gels for Storage or Radioactivity Determination, *Analytical Biochemistry*, 22, 546–549.
K. Wallevik et al., A Simple and Reliable Method for the Drying of Polyacrylamide Slab Gels, *Journal of Biochemical and Biophysical Methods*, 6 17–21 (1982).
S. Joshi et al., Fluorographic Detection of Nucleic Acids Labelled with Weak-Emitters in Gels Containing High Acrylamide Concentrations, *FEBS Letters*, vol. 11S, No. 1, (Aug. 1980).
"The Pharmacia Gel Slab Drier GSD-4 with Heater", Pharmacia Fine Chemicals AB.
"Slab Gel Dryers", Hoefer Scientific Instruments.
"Model 1125B High Capacity Gel Slab Dryer", Bio-Rad Laboratories.
"Model 224 Gel Slab Dryer", Bio-Rad Laboratories.
"Power Cooling Drying", LKB.
Atto Corporation literature–2 pieces.

*Primary Examiner*—Albert J. Makay
*Assistant Examiner*—David W. Westphal
*Attorney, Agent, or Firm*—Townsend and Townsend

[57] ABSTRACT

An apparatus for drying gel slabs supplies heat to a horizontal gel slab from a heating plate above the slab, while drawing a vacuum beneath. The heating plate is weighted and has a flat lower surface at least coextensive with the gel slab. The slab itself is placed on a porous support pad in a vacuum chamber enclosed at the top with a flexible cover which clings to the gel and seals to the perimeter of the chamber when a vacuum is applied from below. The heating plate rests on top of the cover under gravitational force, providing even heating across the entire expanse of the gel slab and for the entire duration of the drying process, resulting in a continuous and uniform vapor flow downward from the gel slab, a minimization of internal stresses, and reduced susceptibility of the gel to cracking.

17 Claims, 4 Drawing Figures

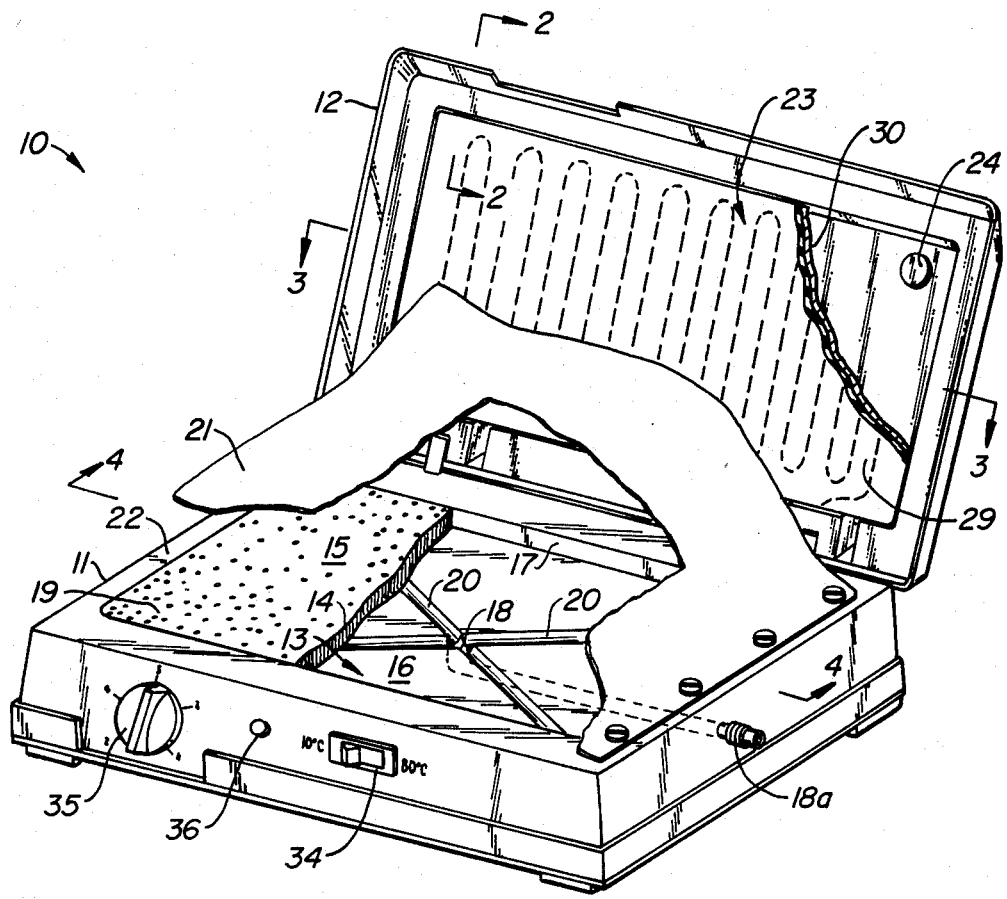
FIG._1.

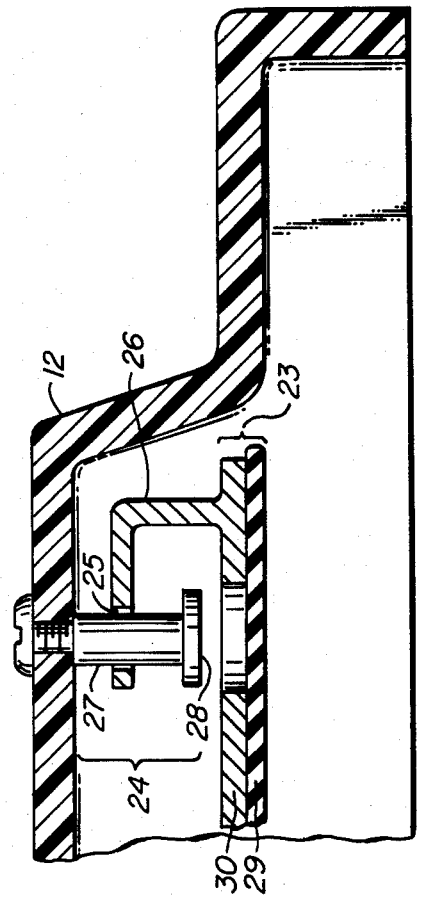
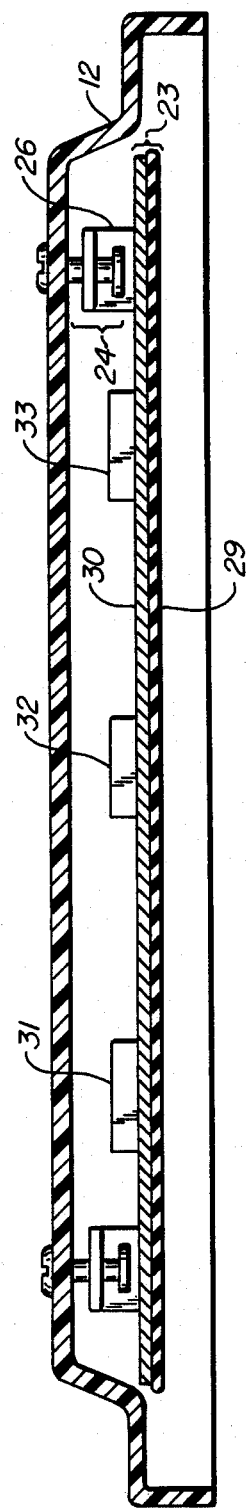

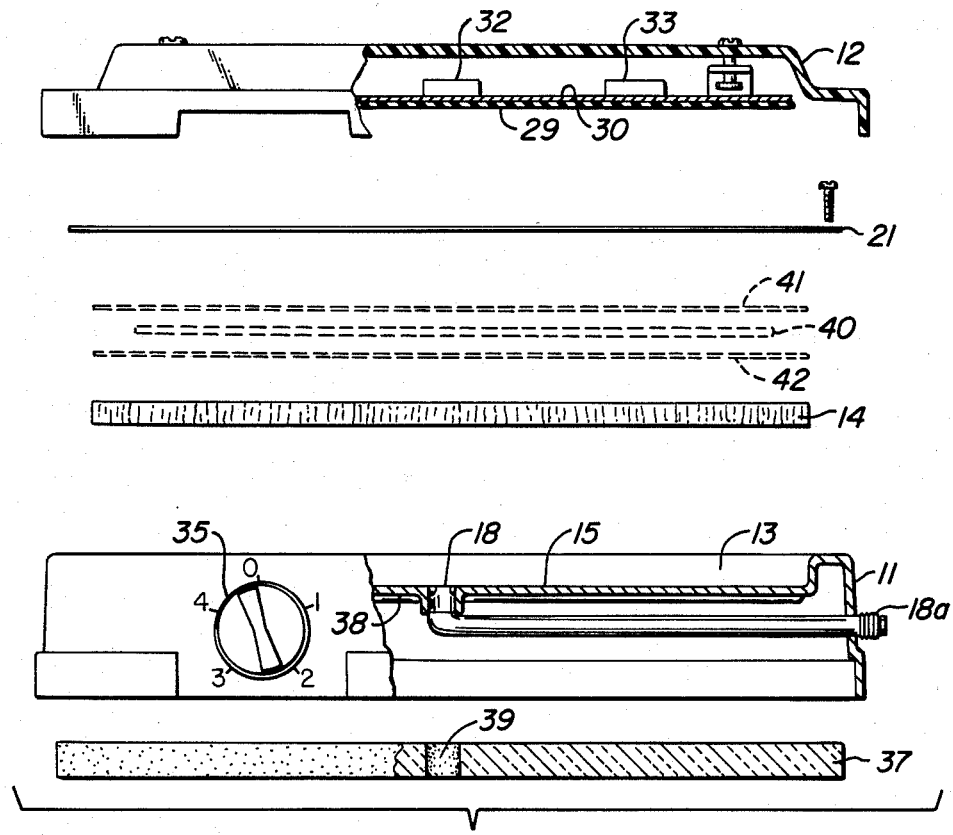
FIG._4.

METHOD AND APPARATUS FOR DRYING GEL SLABS

BACKGROUND OF THE INVENTION

The present invention relates to laboratory techniques and equipment for drying flat gel slabs following electrophoretic separations. In particular, this invention relates to the fixing of gels and the position of the bands therein for purposes of preservation and accurate analysis of the electrophoretic pattern.

Existing devices for the fixing of gel slabs by dehydration generally use both heat and vacuum to vaporize the moisture from the gel. One of several examples in the published literature of such a device is that disclosed in Hoefer, U.S. Pat. No. 4,020,563 (issued May 3, 1977).

The drying of a gel is made difficult by the fact that the gel vitrifies upon drying to a brittle solid impervious to fluid. Thus, when localized heating or vaporization dries a surface or region of a gel slab, moisture in the adjacent regions must find its way around the dried areas in order to escape. Frequently, the moisture can become trapped inside the gel. As the trapped moisture vaporizes and continues to expand, the pressure inside the gel increases and lateral stresses arise, causing the drying gel to crack. In addition, when minute cracks appear, they expand rapidly as the pressurized entrapped vapor seeks release.

SUMMARY OF THE INVENTION

An apparatus and method for drying a gel slab are provided herein, with improved results over the prior art. In both the apparatus and method, a vacuum source placed beneath a horizontally supported gel slab is combined with a weight heating plate resting on top of the slab, compressing the slab with gravitational force. Vaporized moisture leaving the slab flows downward away from the heat source at a uniform rate at all points in the gel slab, and the contact pressure of the heating element is constant throughout the drying process as the gel decreases in thickness. Parallel heat and pressure gradients are maintained to provide even drying of the gel with no trapping of moisture or pressure build-up inside the gel. The result is a substantial improvement in the resistance of a gel slab to cracking during dehydration.

BRIEF DESCRIPTION OF THE DRAWINGS

FIG. 1 is a perspective view of an illustrative drying apparatus according to the present invention with parts broken away, in which the heating plate is incorporated into a hinged lid shown in the open position.

FIG. 2 is a sectional side elevation view of the lid and heating plate of the embodiment of FIG. 1 taken along the line 2—2 thereof.

FIG. 3 is a sectional front elevation view of the lid and heating plate of the embodiment of FIG. 1 taken along the line 3—3 thereof.

FIG. 4 is an exploded front elevation view of the apparatus shown in FIG. 1 taken along the line 4—4 thereof.

DESCRIPTION OF THE PREFERRED EMBODIMENTS

A gel slab dryer 10 representing an illustrative embodiment of the present invention is shown in FIG. 1. The dryer is formed of a base 11 and a lid 12. Both are generally rectangular in shape, the lid being pivotally attached to the base by a hinge connection along one of the long edges, defining the rear of the apparatus.

An open well 13 is formed in the base for receiving a porous support pad 14 with a flat horizontal upper surface 15 of sufficient dimensions to support a wet gel slab. The size and shape of the support pad are not critical provided that its surface 15 is at least coextensive with the gel slab. During a typical drying procedure, the gel is interleaved between protective sheets which extend beyond its edges. In preferred embodiments of the drying apparatus, therefore, the pad surface is both longer and wider than the gel, leaving a margin encircling the gel of sufficient width to accommodate the excess width of the protective sheets.

Since gel slabs used in electrophoresis are generally rectangular, the well 13 and support pad 14 shown in the drawing are also rectangular, the well having a flat bottom surface 16 and straight side walls 17. The bottom surface has a central port 18 through which a vacuum is drawn. The port 18 connects as shown to an exterior tubing connection 18a at the side or rear of the base, for attachment to vacuum tubing leading to a vacuum source. An ordinary laboratory vacuum line may be used. In typical operation, the vacuum is a partial vacuum of at least about 23 inches of mercury (less than about 200 torr absolute pressure).

To achieve a uniform drying rate across the entire surface of the gel slab, the drawing force of the vacuum must be spread out from the vacuum port 18 to span the entire length and width of the gel. To promote this spreading effect, the upper and lower surfaces of the support pad 14 are connected by open pores or passages 19 sufficiently narrow or convoluted to provide flow resistance which will expand the region from which gas or vapor is drawn into the vacuum port. Accordingly, the pad may be constructed of such materials as porous polyethylene or other rigid plastic foams, sintered metal, or bonded glass beads.

In addition, one or more grooves 20 are formed in the bottom surface 16 of the well, extending toward the side walls 17 and opening into the vacuum port 18. These permit vapor flow to the vacuum port with substantially less flow resistance than the pores 19 in the support pad, and thereby tend to maintain a substantially uniform pressure along the bottom of the well while vapor is being drawn through the pad. In preferred embodiments, the grooves are radial and symmetrically arranged around the vacuum port as shown in FIG. 1. As a result, the vaporized moisture leaving the gel is drawn straight down at a uniform rate along the entire lateral expanse of the gel, leaving the gel free of lateral stresses throughout the drying process.

The gel slab with protective layers on both top and bottom is laid flat on top of the support pad 14, with all its edges inside those of the pad. The slab is then covered with a flexible cover sheet 21 in a form of a flap extending over the entire well 13 and overlapping the rim 22 formed by the upper edges of the side walls 17. The cover sheet and the well thus form an enclosed chamber to retain the vacuum. The cover sheet is constructed of a material capable of holding a vacuum yet sufficiently deformable to seal itself around the rim 22 when the pressure inside the chamber is reduced.

The thickness of the support block 14 is such that its upper surface is at a sufficient height to bring the gel in full contact with the cover sheet (through the upper protective layer) before the vacuum is applied. The pressure exerted by the cover sheet on the gel when the chamber is evacuated will then be uniform along the entire contact area between the gel slab and the cover.

The cover 20 is preferably cut from a transparent material to permit the operator of the apparatus to monitor the drying process. An example of such a material is clear silicone rubber. The cover shown in the drawing is secured to the base at one side, permitting one to lift the cover for easy insertion and removal of the support block and gel slab.

The lid 12 of the apparatus supports a floating heating plate 23. The plate is retained in the lid by a loose frictionless attachment which allows the plate a sufficient degree of freedom in the direction perpendicular to the lid such that when the lid is closed, the lower surface of the plate rests on top of the flexible cover 20 under its full gravitational force and no other. One example of such a connection is that shown in the drawings, consisting of a series of posts 24 extending downward from the inside surface of the lid, each to mate with a raised aperture or ring extending upward from the heating plate. In a convenient arrangement, one such post is positioned near each of the four corners of the lid.

One of the four post and ring combinations is shown in detail in FIG. 2. In the embodiment shown, the ring is an aperture 25 in an L-shaped tab 26 extending upward from the heating plate 23 near the corner of the plate. The aperture is of larger diameter than the shaft 27 of the post, providing a loose fit for frictionless sliding of the tab down the shaft. The expanded base of the post 28, being of larger diameter than the aperture 25, limits the path of travel of the arm, thereby retaining the heating plate in the lid as the lid is raised.

The length of each shaft and thus the height range of the heating plate 23 are selected such that when the lid 12 is closed over the base 11, the plate is in contact with the cover sheet 21 and each aperture 25 is spaced apart from both limits of the shaft, remaining so as the gel shrinks in thickness during the drying. Consequently, the heating plate exerts a constant gravitational force on the gel throughout the drying process.

The heating plate 23 and associated controls are shown in FIG. 3. The heating plate may be of any conventional construction which provides substantially even heat transfer to the gel slab. An electrical resistance type heat element, for example, is particularly convenient. Typical such elements may be constructed of electrical wiring woven in between silicone rubber sheets, or any other common construction for a heating pad. In the embodiment shown in the drawings, the plate is of laminated construction, consisting of a planar heating element 29 bonded to a slab of heat conductive material 30 such as aluminum or copper. The slab promotes the uniform distribution of the heat generated by the heating element, and, when placed above the element as shown, communicates the temperature of the element to thermostats 31, 32, 33. The slab 30 also provides mass to the heating plate, adding to the force with which the plate contacts the cover sheet 21 above the gel slab.

The total weight of the plate is not critical and can vary widely. In general, a plate weighing from about 0.5 to about 5 grams per square centimeter of contact surface, preferably from about 0.75 to about 3 grams per square centimeter, will provide the best results. Plates weighing from about 1.1 to about 1.3 grams per square centimeter have been found to be particularly convenient.

Control of the temperature of the heating plate may be achieved according to conventional techniques. The embodiment shown in the drawings contains a series of thermostats 31, 32, 33 to provide the apparatus with flexibility to accommodate the needs of gels of different thicknesses and concentrations. A particularly useful arrangement includes a low heat setting and a high heat setting as well as overheat protection, hence the three thermostats shown. As one example, a low heat thermostat set for 60° C. is suitable for gels to be analyzed by autoradiography, or similar systems which are susceptible to loss of accuracy at higher temperatures, whereas the high level thermostat may be set at 80° C. for use with other systems. The choice of the governing thermostat may be controlled by a switch 34 on the exterior of the apparatus, shown in FIG. 1. The third thermostat may be set to turn off the heater when the temperature exceeds a preset maximum, e.g. 90° C. This serves as overheat protection in the event that the control thermostat which is on line fails. Further optional features include a timer 35 for the heating element and an indicator light 36 showing whether the timer is on or off, thus indicating when the drying sequence is complete.

In FIG. 4, the entire apparatus is shown in an exploded front view, with the lid unhinged, and further including the gel slab and protective layers. In this view, an insulating pad 37 is shown, which fits inside the base 11 up against the underside 38 of the bottom surface of the well 13. The insulating pad contains a hole 39 to accommodate the vacuum conduit. Thus placed, the insulating pad helps the system to retain the heat for more efficient drying.

As shown in FIG. 4, the system is intended for use with a gel slab 40 bounded by protective layers 41 and 42 below and above, respectively, as commonly used in drying and fixing gel slabs. The materials for the protective layers may be those commonly used in the prior art. The lower protective layer is a sheet sufficiently porous to permit vapor flow therethrough, and sufficiently sorptive to bond to the gel as the gel dries. Common laboratory filter paper of various grades or cellophane are generally used. The upper protective sheet 37 may be porous or non-porous, but in any event readily deformable. When the vacuum is applied, the upper sheet will tightly cling to the edges of the gel. When the sheet is fabricated of a porous material such as cellophane, the gel will adhere to it upon drying. The sheet must therefore be clear to permit visual analysis once the drying is completed. Examples of clear nonporous materials are Saran Wrap TM, Glad Wrap TM, and Mylar TM. Nonadherent porous materials such as porous polyethylene or porous polypropylene are removable from the dried gel and thus need not be clear. In general, however, clear materials are preferred for both the upper protective sheet 41 and the cover sheet 21 of the drying apparatus so that the progress of the drying can be visually monitored without disrupting the vacuum. In some instances, the upper protective sheet may be eliminated entirely and the cover sheet 21 may serve as the sole protection for the upper surface of the gel slab.

The foregoing description is offered primarily for illustrative purposes. It will be readily apparent to those skilled in the art that numerous modifications and variations of the materials, construction, and techniques disclosed above may be introduced without departing from the spirit and scope of the invention, as defined by the appended claims.

What is claimed is:

1. Apparatus for drying a horizontally supported gel slab, comprising:
- a weighted heating plate resting evenly on top of said gel slab under gravitational force and at least coextensive therewith;
- a vacuum-retaining sheet interleaved between said heating plate and said gel slab; and
- means for reducing the atmospheric pressure below said gel slab in substantially uniform manner over the surface thereof to draw vaporized moisture downward from said slab.

2. Apparatus according to claim 1 in which said vacuum-retaining sheet is transparent.

3. Apparatus according to claim 1 further comprising a vacuum-retaining chamber enclosing said gel slab and bounded above by said vacuum-retaining sheet.

4. Apparatus according to claim 1 in which the weight of said heating plate is from about 0.5 to about 5.0 grams per square centimeter of surface resting on said gel slab.

5. Apparatus according to claim 1 in which the weight of said heating plate is from about 0.75 to about 3.0 grams per square centimeter of surface resting on said gel slab.

6. Apparatus according to claim 1 in which said heating plate is a laminate comprised of a planar electrical resistance heating element bonded to a slab of heat conductive material.

7. Apparatus according to claim 1 further comprising a vacuum-retaining chamber enclosing said gel slab and bounded above by said vacuum-retaining sheet, and in which said heating plate is retained beneath a lid pivotally attached to said chamber.

8. Apparatus according to claim 1 in which said pressure reducing means is comprised of a vacuum port centrally located beneath said gel slab and a porous support pad disposed between said vacuum port and said gel slab providing sufficient flow resistance to laterally expand the drawing force caused by said vacuum port.

9. Apparatus according to claim 1 further comprising a flat-bottom vacuum-retaining chamber enclosing said gel slab and bounded above by said vacuum-retaining sheet; and said pressure reducing means is comprised of:
- a vacuum port centrally located in the bottom surface of said chamber;
- a porous support pad disposed between said vacuum port and said gel slab, providing sufficient flow resistance to laterally expand the drawing force caused by said vacuum port; and
- at least one groove in said bottom surface of said chamber extending from said vacuum port toward the periphery of said bottom surface to maintain a substantially uniform pressure along said bottom surface.

10. Apparatus for drying a gel slab bounded by a lower protective sheet of sufficient porosity to permit vapor flow therethrough and an upper protective sheet of sufficient flexibility to seal the edges of said gel slab, said apparatus comprising:
- an enclosed chamber defined by a bottom surface, side walls and a transparent flexible cover capable of forming a seal with said side walls upon the reduction of pressure inside said chamber;
- means for evacuating said chamber through said bottom surface;
- a porous support pad sized to fit inside said chamber and of sufficient thickness to support said gel slab with said upper protective sheet in contact with said flexible cover; and
- a weighted heating plate at least coextensive with said gel slab resting evenly on top of said cover under gravitational force.

11. Apparatus for drying a gel slab and for fixing said slab to a lower porous sheet while protected by a transparent deformable upper protective sheet capable of sealing the top surface and side edges of said gel slab against gas flow when a vacuum is drawn from below, said apparatus comprising:
- an enclosed chamber defined by a flat heat-insulated bottom surface, side walls, and a transparent flexible cover capable of sealing to said side walls upon the reduction of pressure inside said chamber;
- a vacuum port centrally located in said bottom surface;
- a porous support pad sized to fit inside said chamber and of sufficient thickness to support said gel slab with said upper protective sheet in contact with said flexible cover, providing sufficient flow resistance to laterally expand the drawing force of a vacuum pulled through said vacuum port;
- a plurality of grooves in said bottom surface extending radially from said vacuum port toward said side walls to maintain a substantially uniform pressure along said bottom surface;
- a weighted laminated heating plate at least coextensive with said gel slab, comprised of a planar electrical resistance heating element bonded to a slab of heat conductive material; and
- a lid pivotally attached to said chamber, loosely retaining said heating plate therein with sufficient freedom of motion that when said lid is closed, said heating plate rests evenly on said flexible cover under gravitational force.

12. Method for drying a gel slab and bonding said gel slab to a porous sheet, said method comprising:
 (a) laying said gel slab flat over said porous sheet;
 (b) laying said porous sheet flat over a porous horizontal support surface;
 (c) covering said gel slab with a deformable protective sheet capable of sealing the top surface and side edges of said gel slab against gas flow when a vacuum is drawn from below;
 (d) drawing a vacuum downward through said porous support surface; and
 (e) heating the upper surface of said gel slab with a weighted heating plate at least coextensive with said gel slab and resting evenly thereon under gravitational force, until substantially no moisture remains in said slab.

13. Method according to claim 12 in which the weight of said weighted heating plate is from about 0.5 to about 5.0 grams per square centimeter of surface resting on said gel slab.

14. Method according to claim 12 in which the weight of said weighted heating plate is from about 0.75 to about 3.0 grams per square centimeter of surface resting on said gel slab.

15. Method according to claim 12 in which said deformable protective sheet is transparent.

16. Method according to claim 12 in which the degree of vacuum in step (d) is less than about 200 torr absolute pressure.

17. Apparatus for drying a horizontally supported gel slab, comprising:

a vacuum-retaining chamber enclosing said gel slab and bounded above by a transparent vacuum-retaining sheet;

a lid pivotally attached to the top of said vacuum-retaining chamber;

a weighted heating plate retained in said lid by a plurality of posts each slidably engaged by a loose-fitting aperture; and means for reducing the atmospheric pressure below said gel slab in substantially uniform manner over the surface thereof to draw vaporized moisture downward from said slab.

* * * * *